United States Patent [19]
Jiang et al.

[11] Patent Number: 6,150,581
[45] Date of Patent: *Nov. 21, 2000

[54] CHITOSAN/ALGINATE ANTI-ADHESION BARRIER

[75] Inventors: Ying Jiang, North Haven; Mark S. Roby, Killingworth, both of Conn.

[73] Assignee: United States Surgical Corporation, Norwalk, Conn.

[*] Notice: This patent issued on a continued prosecution application filed under 37 CFR 1.53(d), and is subject to the twenty year patent term provisions of 35 U.S.C. 154(a)(2).

Under 35 U.S.C. 154(b), the term of this patent shall be extended for 645 days.

[21] Appl. No.: 08/480,082

[22] Filed: Jun. 7, 1995

[51] Int. Cl.[7] .............................. A61F 13/00; A61B 17/08
[52] U.S. Cl. .............................................. 602/50; 606/214
[58] Field of Search ................................. 602/48–52, 902, 602/904; 604/890.1; 606/213–215; 623/901

[56] References Cited

U.S. PATENT DOCUMENTS

| | | |
|---|---|---|
| 2,441,729 | 5/1948 | Steiner . |
| 3,632,754 | 1/1972 | Balassa . |
| 3,903,268 | 9/1975 | Balassa . |
| 3,911,116 | 10/1975 | Balassa . |
| 4,185,618 | 1/1980 | Corey . |
| 4,326,532 | 4/1982 | Hammar . |
| 4,378,017 | 3/1983 | Kosugi et al. . |
| 4,394,373 | 7/1983 | Malette et al. . |
| 4,452,785 | 6/1984 | Malette et al. . |
| 4,532,134 | 7/1985 | Malette et al. . |
| 4,572,906 | 2/1986 | Sparkes et al. . |
| 4,603,695 | 8/1986 | Ikada et al. . |
| 4,659,700 | 4/1987 | Jackson . |
| 4,674,488 | 6/1987 | Nashef et al. . |
| 4,808,707 | 2/1989 | Daly et al. . |
| 4,840,626 | 6/1989 | Linsky et al. . |
| 4,911,926 | 3/1990 | Henry et al. . |
| 4,946,870 | 8/1990 | Partain, III et al. . |
| 4,952,618 | 8/1990 | Olsen . |
| 4,956,350 | 9/1990 | Mosbey . |
| 5,093,319 | 3/1992 | Higham et al. . |
| 5,112,903 | 5/1992 | Sakakibara et al. ................ 525/54.2 |
| 5,116,747 | 5/1992 | Moo-Young et al. . |
| 5,126,141 | 6/1992 | Henry .................................. 424/423 |
| 5,200,180 | 4/1993 | Bannert . |
| 5,266,326 | 11/1993 | Barry et al. . |
| 5,312,333 | 5/1994 | Churinetz et al. . |
| 5,318,780 | 6/1994 | Viegas et al. . |
| 5,460,939 | 10/1995 | Hansbrough et al. ................ 435/1.1 |
| 5,492,982 | 2/1996 | Shimizu et al. ........................ 526/62 |
| 5,508,036 | 4/1996 | Bakker et al. ........................ 424/424 |
| 5,531,735 | 7/1996 | Thompson ........................ 604/890.1 |
| 5,575,815 | 11/1996 | Slepian et al. ........................... 623/1 |
| 5,580,923 | 12/1996 | Yeung et al. ........................ 525/54.1 |
| 5,587,175 | 12/1996 | Viegas et al. ......................... 424/427 |
| 5,738,860 | 4/1998 | Schonfeldt et al. ................. 424/402 |
| 5,759,570 | 6/1998 | Arnold ................................. 604/304 |

FOREIGN PATENT DOCUMENTS

| | | |
|---|---|---|
| 0152898 | 2/1985 | European Pat. Off. . |
| 0187703 | 7/1986 | European Pat. Off. . |
| 0262890 | 4/1988 | European Pat. Off. . |
| 0372969 | 6/1990 | European Pat. Off. . |
| 8600912 | 2/1986 | WIPO . |

OTHER PUBLICATIONS

Windholz (editor) et al., The Merck Index, pp.273–274, 286–287, 314, 1983.

*Primary Examiner*—Sharon Kennedy

[57] ABSTRACT

Chitosan/alginate post-surgical anti-adhesion barriers, methods of preventing post-surgical adhesions, and methods and devices for forming post-surgical anti-adhesion barriers are provided. An aqueous solution of chitosan and a complexing agent, and an aqueous solution of alginate are combined to form an anti-adhesion barrier at a site of surgical intervention. A medicinal agent may optionally be incorporated.

18 Claims, 2 Drawing Sheets

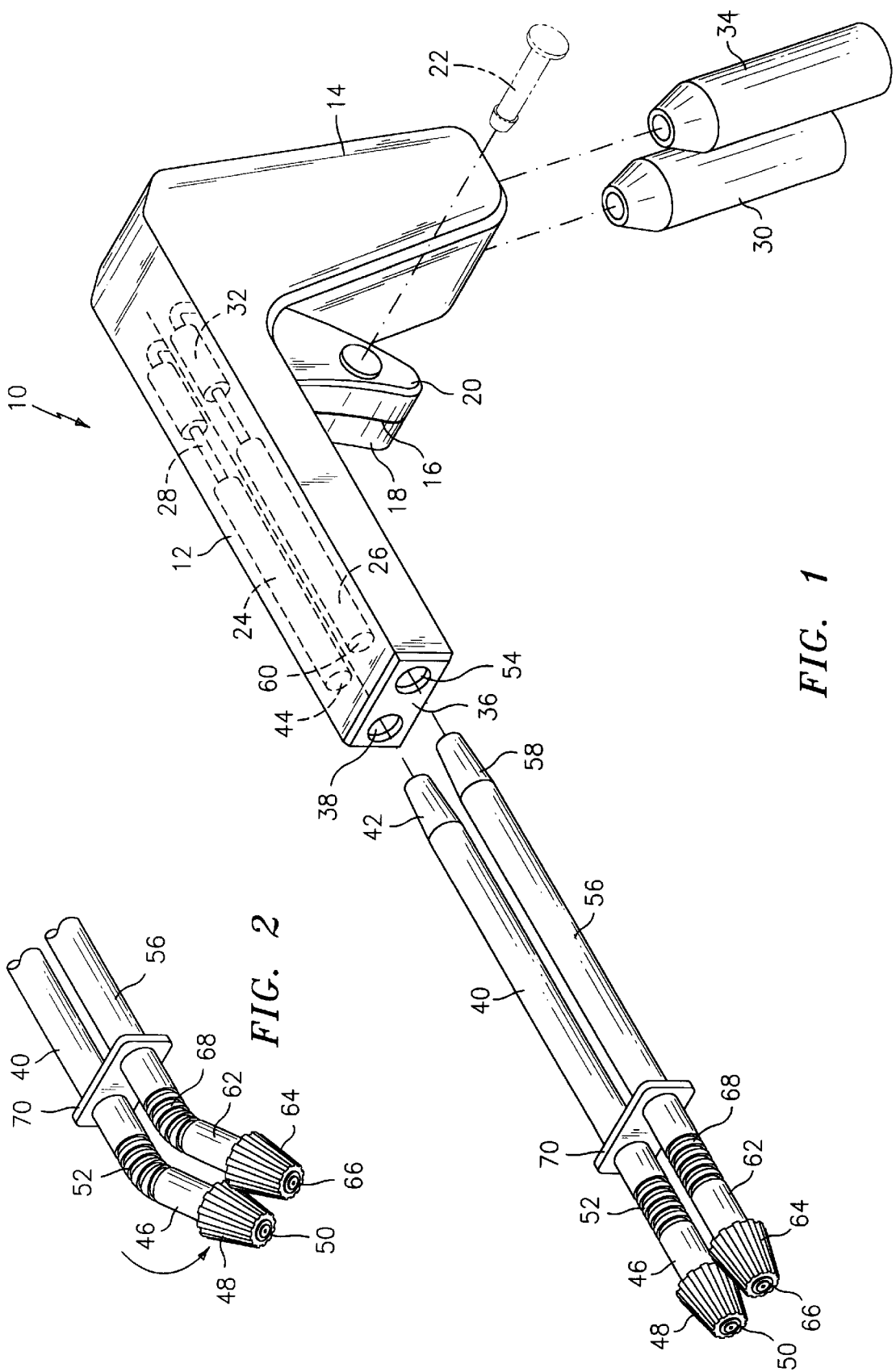

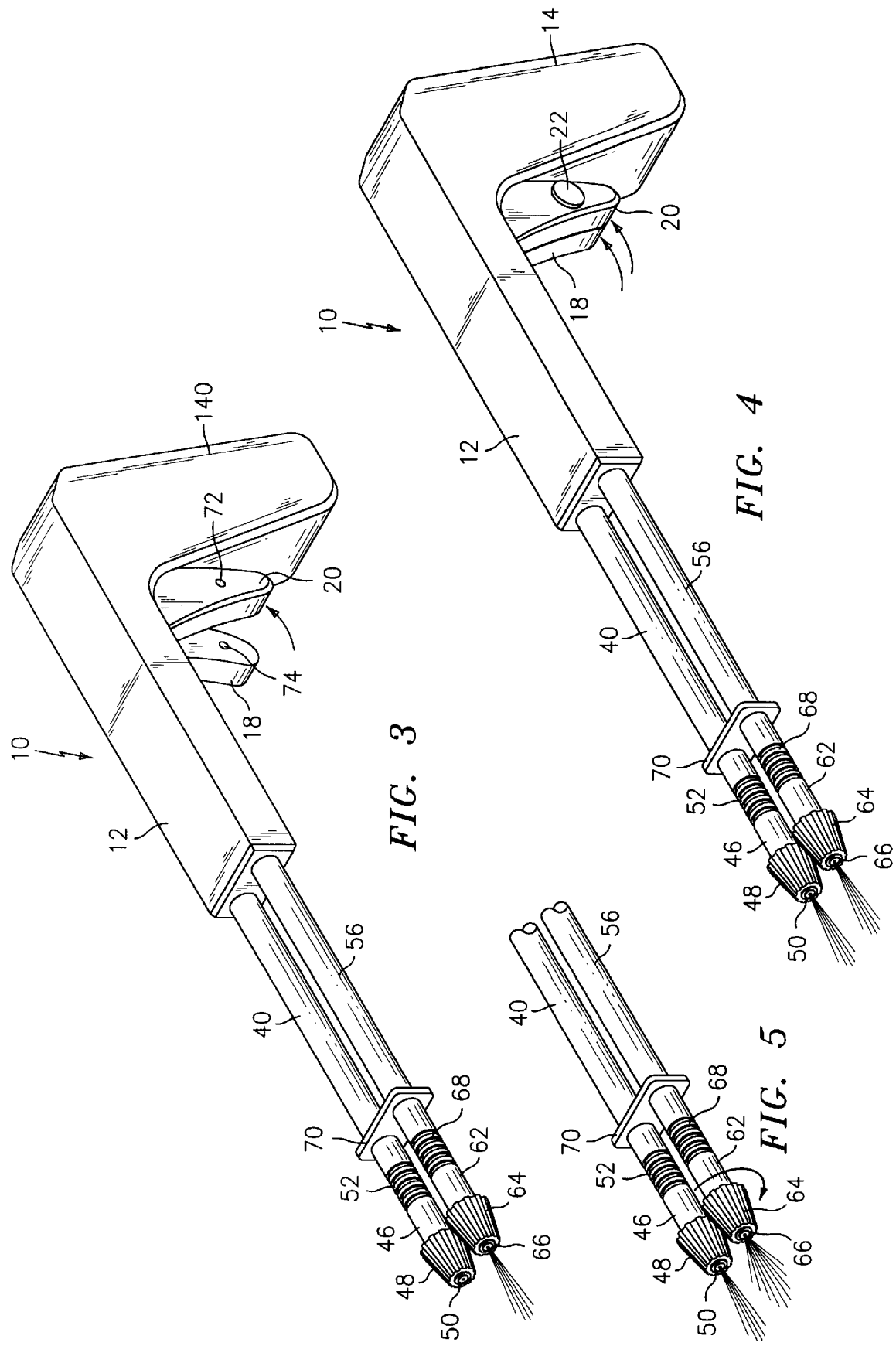

CHITOSAN/ALGINATE ANTI-ADHESION BARRIER

BACKGROUND

1. Technical Field

The present disclosure relates to prevention of post-surgical adhesions and more particularly, to devices and methods for preventing the formation of such adhesions between a healing trauma site and adjacent surrounding tissue.

2. Background of Related Art

Injury, surgical incision or abrasion to the peritoneum, pleural or abdominal cavity results in an outpouring of a serosanguinous exudate. The exudate subsequently coagulates, producing fibrinous bands between abutting surfaces which can become organized by fibroblast proliferation to become collagenous adhesions. Adhesions are also known to form at bone fracture sites where jagged, irregular bone edges form in the area of the fracture. Bony spurs promote the growth of fibrous adhesions between the bone fracture surface and surrounding tissue.

Adhesion formation following surgery or trauma is generally considered to be undesirable. For example, adhesions that form in relation to intestinal surgery, e.g., bowel resection, hernia repair, etc. may cause obstruction of the intestine. Adhesions that form near the bone fracture site may reduce or hinder the normal movement of the area of repair by restricting the natural movement of tendons over the adjacent bone. Adhesions may also form in the vicinity of nerves and disrupt nerve transmissions with a resultant diminution of sensory or motor function.

Various methods and substances have been used in the hope of preventing post-operative adhesions. Certain drugs and surfactants have been suggested. For example, U.S. Pat. No. 4,911,926 is directed to adhesion prevention by application of aqueous and non-aqueous compositions of a polyoxyalkylene block copolymer to injured areas of the peritoneal or pleural cavity or organs situated therein subsequent to surgical injury.

Another approach to adhesion prevention involves application of a physical barrier at the area of surgical injury. U.S. Pat. No. 4,674,488 is directed to interposing a barrier layer of soft biological tissue, such as collagen, collagen-fabric films, collagen membranes, or reconstituted collagen or Dacron® mesh, at the interface of a bone fracture and the surrounding tissue. U.S. Pat. No. 4,603,695 is directed to a molded adhesion barrier of a biodegradable polymer such as polyester, collagen, amino acid polymers and chitin placed where there is a possibility of adhesion setting in.

Other materials have also been used to form physical barriers in an attempt to prevent adhesions, including silicone elastomers, gelatin films and knit fabrics of oxidized regenerated cellulose (hereinafter ORC). In some cases, it is suggested that heparin, heparinoid, or hexuronyl hexosaminogly can be incorporated into a matrix of ORC fabric or other matrices of hyaluronic acid, cross-linked and uncross-linked collagen webs, synthetic resorable polymers, gelatin films, absorbable gel films, oxidized cellulose fabrics and films which are fabricated into a form that is said to be drapable, conformable and adherent to body organs and substantially absorbable within 30 days. See, e.g., U.S. Pat. No. 4,840,626 or EPA Pub. No. 0 262 890 or EPA Pub. No. 0 372 969.

Alginate and chitosan have been used in an attempt to prevent adhesions, cause hemostasis, or to fill wounds. For example, U.S. Pat. No. 5,266,326 describes in situ modification of alginate, i.e., modification while in the intra-articular space to prevent adhesions formed post-operatively. As discussed therein, adhesions are prevented by simultaneous injection of alginate solution and a complexing solution into the intra-articular space following closure of the surgical site. Examples given of the complexing solution are calcium chloride, MgCl, and $CaSO_4$. A method of achieving hemostasis in open wounds by placing chitosan, in liquid or powder form, in contact with the wound is described in U.S. Pat. No. 4,394,373. Wound filling gel-like compositions made of chitosan and hydrocolloid materials taken from locust bean gum, karaya gum, guar gum and derivatives of guar gum are described in U.S. Pat. No. 4,956,350.

Chitosan and alginate have been used together for sustained release of pharmaceutically active agents and immobilization of biologically active material. A sustained release preparation is described in European Patent Application Pub. No. 0 187 703. As discussed therein, the preparation contains chitosan, at least one anionic polymer compound which may include alginic acid, and at least one pharmaceutically active agent. U.S. Pat. No. 5,116,747 is directed to immobilization of biologically active material in capsules prepared from a water-soluble polymer and chitosan acetate. As described therein, biological cells are encapsulated, entrapped or occluded within an ionically-interacted combination of chitosan and alginate. European Patent Application Pub. No. 0 152 898 is directed to a process for encapsulation and encapsulated active material system. As described therein, cells, microorganisms, or nonbiochemicals are encapsulated by a polymer complex of the combination of an anionic polymer such as alginate and a cationic polymer such as chitosan.

SUMMARY

A method of preventing post-surgical adhesions is provided which includes providing an aqueous solution of chitosan and a complexing agent, providing an aqueous solution of alginate, and combining the chitosan/complexing agent solution with the alginate solution to form an anti-adhesion barrier at a site of surgical intervention. In one embodiment, the chitosan/complexing agent solution and the alginate solution are combined by spraying each solution onto a target site. The chitosan/complexing agent solution and the alginate solution may be sprayed simultaneously by separate sprayers. A medicinal agent may optionally be incorporated into the chitosan/complexing agent solution, the alginate solution, or both solutions.

In another aspect, a post-surgical anti-adhesion barrier delivery device includes a first sprayer containing an aqueous solution of chitosan and a complexing agent, a second sprayer containing an aqueous solution of alginate, and an actuator which causes the first sprayer and the second sprayer to spray. A medicinal agent may optionally be incorporated into the chitosan/complexing agent solution, the alginate solution, or both solutions.

In another aspect, a method of forming a post-surgical anti-adhesion barrier is provided which includes providing an aqueous solution of chitosan and a complexing agent, providing an aqueous solution of alginate and combining the chitosan/complexing agent solution with the alginate solution to form a post-surgical anti-adhesion barrier at a site of surgical intervention. In one embodiment, the chitosan/complexing agent solution and the alginate solution are combined by spraying each solution onto a target site. The two solutions may be sprayed simultaneously by separate sprayers. A medicinal agent may optionally be incorporated into the chitosan/complexing agent solution, the alginate solution, or both solutions.

BRIEF DESCRIPTION OF THE DRAWINGS

FIG. 1 is a perspective view with parts broken away of a sprayer device for delivery of a chitosan/complexing agent solution and an alginate solution.

FIG. 2 is a perspective partial view showing rebendable members of the sprayer device illustrated in FIG. 1.

FIG. 3 is a perspective view of the assembled sprayer device illustrated in FIG. 1 showing operation of one sprayer.

FIG. 4 is a perspective view showing operation of the assembled sprayer device illustrated in FIG. 1.

FIG. 5 is a perspective partial view showing variable spray density in operation of the sprayer device illustrated in FIG. 1.

DETAILED DESCRIPTION OF PREFERRED EMBODIMENTS

Post-surgical anti-adhesion barriers, methods of preventing post-surgical adhesions, and methods and devices for forming post-surgical anti-adhesion barriers are provided. Chitosan/alginate anti-adhesion barriers as described herein prevent formation of post-surgical adhesions at a wound or trauma site by interposing a unique biocompatible, bioabsorbable barrier between damaged tissue and adjacent surrounding tissue. As described in more detail below, the anti-adhesion barrier is formed and applied by pouring or spraying a solution of chitosan and complexing agent and a solution of alginate to a site of surgical intervention.

Chitosan is a polycationic material having pendent amine groups. It is biocompatable, biodegradable, mechanically stable, and water soluble. The ability to use water as a solvent is advantageous since it avoids use of toxic or irritating organic solvents. Preferred forms of chitosan include salts of chitosan such as chitosan malate and chitosan glutamate, which are relatively soluble in water.

A first solution is formed by dissolving chitosan in acidic water in an amount ranging from about 1% to about 10% by weight. The pH of the solution is preferably greater than or equal to about 5. Organic or inorganic acids may be used to control pH including acetic acid, hydrochloric acid, formic acid, nitric acid and sulfuric acid. Acetic acid is preferred.

A complexing agent is then added to the solution. Alternatively, chitosan is added to a solution of complexing agent and water. The complexing agent does not complex with the chitosan, but is present to assist in formation of a hydrogel when the first solution is combined with a second solution containing alginate as described below. Suitable complexing agents are calcium salts such as calcium chloride and calcium sulfate, and magnesium salts such as magnesium chloride and magnesium sulfate. The concentration of complexing agent in the first solution ranges from about 1% to about 5% by weight. The chitosan and complexing agent are mixed with water in any manner known to those with skill in the art. Distilled water, sterile water and bacteriostatic water are suitable for use herein. The first solution may be made isotonic if desired.

A second solution is formed by dissolving alginate in water in an amount ranging from about 1% to about 10% by weight. Alginates are the salt and ester forms of alginic acid. Alginate is a polymer made up of guluronic acid and mannuronic acid. By varying the amount of guluronic acid and mannuronic acid present in alginate, physical properties such as gel strength and film forming properties are varied. Stronger films result from a higher relative concentration of guluronic acid. Naturally occurring alginates with known varying concentrations of guluronic acid and mannuronic acid are commercially available. The molecular weight of the alginates used herein may range from about 200,000 to several million depending on the source of the alginate. Alginate is a polyanionic polymer having functionalized carboxyl groups. Preferred alginate salts for use herein are sodium and potassium salts. Methods of dissolving alginate in water are well-known by those with skill in the art. As above, distilled water, sterile water and bacteriostic water are suitable for use herein. The second solution may also be made isotonic.

The first solution is combined with the second solution to form an anti-adhesion barrier at a suitable location. Chitosan, being cationic, interacts with the anionic alginate, i.e., the amino groups of the chitosan and the carboxyl groups of the alginate undergo ionotrophic gelation and formation of a stable, biodegradable hydrogel. The complexing agent provides divalent cations which also interact with alginate to cause gelation. The alginate anion, the chitosan cation and the complexing agent act together to form an especially durable, biodegradable structure.

In one embodiment, the first solution and second solution are poured into an area of surgical intervention and mix in situ to form a hydrogel anti-adhesion barrier. In a more preferred embodiment, the first solution and second solution are sprayed to a target site and, depending on the orientation of their respective sprayers, will mix in the air stream and/or on contact with surface at the target site. To accomplish this, the first solution is contained in a first sprayer and the second solution is contained in a second sprayer. The two sprayers may be actuated together by a common actuator or independently by an actuator having separate respective sub-actuators operatively connected to each sprayer. Adjustable valves on the sprayer tips allow the spray volume of the first or second solutions to be varied, thus regulating the concentration of first solution relative to the second solution. The spray heads of the sprayer may be directionally orientable to assist in providing overlapping or separate spray streams. An endoscopic material delivery device suitable for separately delivering the first and second solutions is described in U.S. Pat. No. 5,312,333, the disclosure of which is incorporated herein by reference.

Referring now to FIG. 1, a delivery device is illustrated which allows the first solution and the second solution to be conveniently delivered separately or simultaneously to target sites. The delivery device 10 includes a pistol-like handle having a longitudinal barrel portion 12 and a hollow grip portion 14 depending transversely from the barrel portion 12. Grip portion 14 may have any configuration which can be easily and comfortably gripped. An actuator portion 16 includes a movable first trigger 18 and a movable second trigger 20 which depend transversely from the barrel portion 12. A removable pin 22 fits into a bores 72 and 74 (shown in FIG. 3) extending through the first trigger 18 and second trigger 20.

The top of the barrel portion 12 is removable to allow access to the interior of the barrel portion 12. The interior of the barrel portion is configured to receive and hold a removable first cartridge 24 which contains either the first solution or the second solution, and a removable second cartridge 26 which contains either the first solution or the second solution. A first conduit 28 in the barrel portion 12 is reattachably connected at one end to the first cartridge 24 and, at its other end, is connected to a reattachable first compressed gas canister 30. A second conduit 32 in the barrel portion 12 is reattachably connected at one end to the second cartridge 26 and, at its other end, is connected to a reattachable second canister 34. The first and second conduits 28 and 32 conduct compressed gas from the first and second canisters 30 and 34 to the first and second cartridges 24, respectively. The first and second triggers 18 and 20 are each mechanically linked to the canisters 30 and 34, respectively, in a manner known, such as that described in U.S. Pat. Nos. 5,312,333 and 4,349,028, both disclosures being herein incorporated by reference. Actuation of the first trigger 18 releases compressed gas from the first canister 30 and actuation of the second trigger 20 releases compressed gas from the second canister 34.

A proximal end 36 of the barrel portion 12 includes a first port 38 for receiving a first shaft 40. A first tapered proximal end 42 of the first shaft 40 may be inserted through the first port 38 so as to be frictionally or mechanically engaged therein. The first shaft 40 is formed with an axial passageway through which the solution contained in the first cartridge 24 can pass. The first tapered proximal end 42 mates with an outlet 44 of the first cartridge 24 to form a contiguous connection between the first cartridge 24 and the first shaft 40. The distal end 46 of the first shaft 40 includes a first valve 48 and spray head 50 which may be adjusted to vary the form of the solution exiting the spray head 50 from a stream to a fine spray to an off or non-spraying position. The valve 48 may also be used to adjust the volume of solution exiting the spray head 50 and can be used to vary the concentration of first solution in relation to second solution. The distal end 46 of the first shaft 40 also includes a rebendable member 52 which allows the distal end 46 to be bent, i.e., the spray head 50 is directionally orientable to direct solution exiting the first shaft 40 in desired directions and can be used, e.g., to cause first solution and second solution to intersect and mix in the air prior to contacting a target surface.

The proximal end 36 of the barrel portion 12 also includes a second port 54 for receiving a second shaft 56. A second tapered proximal end 58 of the second shaft 56 may be inserted through the second port 54 so as to be frictionally engaged therein. The second shaft 56 is formed with an axial passageway through which the solution contained in the second cartridge 26 can pass. The second tapered proximal end 58 mates with an outlet 60 of the second cartridge 26 to form a contiguous connection between the second cartridge 26 and the second shaft 56. The distal end 62 of the second shaft 56 includes a second valve 64 and spray head 66 which may be adjusted to vary the form of the solution exiting the spray head 66 from a stream to a fine spray to an off or non-spraying position. The second valve 64 may also be used to adjust the volume of the solution exiting the spray head 50 and may be used to vary the concentration of first solution in relation to second solution. The distal end 62 of the second shaft 56 also includes a rebendable member 68 which allows the distal end 62 to be bent, i.e., the spray head 66 is directionally orientable to direct the solution exiting the second shaft 56 in desired directions and can be used, e.g., to cause first and second solutions to intersect and mix in the air prior to contacting a target surface. A stabilizer member 70 keeps the first shaft 40 and the second shaft 56 in substantially parallel alignment.

FIGS. 3 and 4 illustrate certain aspects of operation of the delivery device 10. In operation, either first trigger 18, second trigger 20, or both may be depressed to cause compressed gas to exit canister 30, canister 34, or both. When the pin 22 is removed from bores 72 and 74, the first trigger 18 and second trigger 20 operate independently of one another. In this manner, if the first cartridge 24 contains first solution and the second cartridge 26 contains second solution, by depressing only the first trigger 18, the first solution is dispensed from the delivery device 10. If only the second trigger 20 is depressed, only the second solution is dispensed from the delivery device 10. This is because the first trigger 18 releases compressed gas from the first canister 30 which flows to the first cartridge 24 in such a manner as to exert force on the rear end of the first cartridge 24, thereby causing a metered quantity of first solution to be dispensed. When the second trigger 20 is depressed, compressed gas from the second canister 34 is conducted through the second conduit 32 in such a manner as to exert force on the rear end of the second cartridge 26, thereby causing a metered quantity second solution to be dispensed. When pin 22 is engaged in both bores 72 and 74, both triggers 18 and 20 are actuated simultaneously, thus dispensing first solution and second solution simultaneously.

The adjustable valves 48 and 64 allow the spray volume and dispersion range of the solution exiting the spray heads 50 and 66 to be varied as depicted, for example in FIG. 5. The second trigger 20 is shown depressed in FIG. 3, thus illustrating actuation and dispensation of solution out of the second spray head 66. The direction of either solution or both solutions may be changed by bending rebendable members 52 and 68 in tandem, as is illustrated in FIG. 2, or separately in different directions at the option of the user.

It should be understood that the delivery device 10, as illustrated, is an exemplification and that other delivery mechanisms such as those described in U.S. Pat. No. 5,312,333 may be incorporated. For example, a manually activated plunger mechanism may be utilized in place of the compressed air system described above to separately dispense solution from the cartridges. It is also contemplated that any other spray mechanisms may be utilized such as pump and spray mechanisms found in common water guns or in cleaning fluid spray bottles. Aerosol sprayers may also be utilized.

The barrier formed by pouring or spraying is a film which conforms to the underlying terrain of the tissue to which it is applied. The hydrophilic nature of the resulting film causes the film to adhere well to tissue.

Regardless of how the first and second solutions are combined, the proportion of first solution to second solution ranges from about 1:1 to about 1:10 and is preferably about 1:2 or 1:3. The ability of a chitosan/alginate adhesion barrier to combine at or near the target site provides certain advantages. For example, the barrier provides custom fit in the area of surgical intervention. The barrier may also be applied endoscopically to surgical target sites, i.e., long stemmed spraying devices can be inserted into the peritoneal cavity or into other locations in the body through cannulas in minimally invasive surgical procedures. The resulting antiadhesion barrier forms a physical barrier between tissues to prevent attachment of adhesions. The chitosan/alginate antiadhesion barrier is biodegradable and is thus absorbed over time, obviating the need for subsequent surgery to remove the barrier. Since the solvent used is water, there is little or no irritation at the site of application.

In another aspect, the barrier formed by combining chitosan and alginate, as described herein, can be used as a topical wound protectant by applying the two solutions described above to a wound located inside the body or on a wound exposed to the surface.

In another aspect, one or more medicinal agents are incorporated into the anti-adhesion barrier. Suitable medicinal agent(s) may be added to the first solution, the second solution, or both solutions prior to combination. It should be understood that the medicinal agent must not adversely interact with chitosan or alginate. For example, a medicinal agent that is strongly cationic would cause premature gelation of alginate and is thus added to the chitosan/complexing agent solution. Similarly, strongly anionic medicinal agents should be added to the alginate solution and not the chitosan/complexing agent solution.

The term "medicinal agent", as used herein, is meant to be interpreted broadly and includes any substance or mixture of substances which may have any clinical use in medicine. Thus medicinal agents include drugs, enzymes, proteins, peptides, glycoproteins, or diagnostic agents such as releasable dyes which may have no biological activity per se.

Examples of classes of medicinal agents that can be used include antimicrobials, analgesics, antipyretics, anesthetics, antiepileptics, antihistamines, anti-inflammatories, anti-clotting agents, cardiovascular drugs, diagnostic agents, sympathomimetics, cholinomimetics, anti-muscarinics, antispasmodics, hormones, growth factors, muscle relaxants, adrenergic neuron blockers, anti-neoplastics, immunosuppressants, gastrointestinal drugs, diuretics, steroids and enzymes. It is also intended that combinations of medicinal agents can be used.

By incorporating a medicinal agent(s) into a chitosan/alginate anti-adhesion barrier, focal delivery and application of a medicinal agent(s) to the wound site is achieved. Focal application may be more desirable than general systemic application in some cases, e.g., chemotherapy for localized tumors, because it produces fewer side effects in distant tissues or organs and also concentrates therapy at intended sites. Focal application of growth factors, anti-inflammatories, immune system suppressants and/or antimicrobials by the anti-adhesion barrier is an ideal drug delivery system to speed healing of a wound or incision. Delivery of suitable anti-clotting agents aids in preventing fibroblast formation, thus augmenting the effect of the physical barrier in preventing post-surgical adhesions. The medicinal agent(s) diffuse from the hydrogel barrier and/or are released as the barrier is biodegraded and absorbed.

The following examples are included for purposes of illustration and are not intended to limit the disclosure herein.

EXAMPLE 1

10 gm of food grade sodium alginate (commercially available from Pronova Biopolymer, Inc. of Portsmouth, N.H.) was dissolved in 400 ml of distilled water. The solution was stirred at room temperature for 24 hours and then filtered using filter paper with vacuum suction. The resulting solution was labeled Solution 1.

EXAMPLE 2

10 gm of chitosan (commercially available from Pronova Biopolymer, Inc. of Portsmouth, N.H.) was added to 550 ml of 1% acetic acid aqueous solution. After the chitosan dissolved, 10 gm calcium chloride was added with stirring. The solution was filtered. The resulting solution was labeled Solution 2.

EXAMPLE 3

Approximately 2 to 3 ml of Solution 1 was sprayed onto a 2×2 inch defect on a dog's abdominal wall using an air brush equipped with a propane gas can. Thereafter, 0.5 to 1 ml of Solution 2 was sprayed onto Solution 1. A solid hydrogel film formed immediately and covered the defect.

It will be understood that various modifications may be made to the embodiments and aspects disclosed herein. Therefore the above description should not be construed as limiting, but merely as exemplifications of preferred embodiments. Those skilled in the art will envision modifications within the scope and spirit of the claims appended hereto.

What is claimed is:

1. A method of preventing post-surgical adhesions comprising:

providing an aqueous solution of chitosan and a complexing agent;

providing an aqueous solution of alginate; and combining the chitosan/complexing agent solution with the alginate solution to form an anti-adhesion barrier at a site of surgical intervention.

2. A method according to claim 1 wherein the chitosan/complexing agent solution contains from about 1% to about 10% by weight chitosan.

3. A method according to claim 2 wherein the chitosan/complexing agent solution contains from about 1% to about 5% by weight complexing agent.

4. A method according to claim 3 wherein the complexing agent is selected from the group consisting of calcium chloride, calcium sulfate, magnesium chloride and magnesium sulfate.

5. A method according to claim 1 wherein the alginate solution contains from about 1% to about 10% by weight alginate.

6. A method according to claim 1 wherein the proportion of chitosan/complexing agent solution to alginate solution ranges from about 1:1 to about 1:10.

7. A method according to claim 1 wherein the chitosan/complexing agent solution and the alginate solution are combined by spraying each solution onto a target site at the site of surgical intervention.

8. A method according to claim 7 wherein the chitosan/complexing agent solution and the alginate solution are sprayed simultaneously by separate sprayers.

9. A method according to claim 1 wherein a medicinal agent is added to the chitosan/complexing agent solution, the alginate solution, or both solutions.

10. A method of forming a post-surgical adhesion barrier comprising:

providing an aqueous solution of chitosan and a complexing agent;

providing an aqueous solution of alginate; and combining the chitosan/complexing agent solution with the alginate solution to form an anti-adhesion barrier at a site of surgical intervention.

11. A method according to claim 10 wherein the chitosan/complexing agent solution contains from about 1% to about 10% by weight chitosan.

12. A method according to claim 11 wherein the chitosan/complexing agent solution contains from about 1% to about 5% by weight complexing agent.

13. A method according to claim 12 wherein the complexing agent is selected from the group consisting of calcium chloride, calcium sulfate, magnesium chloride and magnesium sulfate.

14. A method according to claim 10 wherein the alginate solution contains from about 1% to about 10% by weight alginate.

15. A method according to claim 10 wherein the proportion of chitosan/complexing agent solution to alginate solution ranges from about 1:1 to about 1:10.

16. A method according to claim 10 wherein the chitosan/complexing agent solution and the alginate solution are combined by spraying each solution onto a target site at the site of surgical intervention.

17. A method according to claim 10 wherein the chitosan/complexing agent solution and the alginate solution are sprayed simultaneously by separate sprayers.

18. A method according to claim 10 wherein a medicinal agent is added to the chitosan solution, the alginate solution, or both solutions.

* * * * *